United States Patent [19]
Nichols

[11] Patent Number: 5,206,022
[45] Date of Patent: Apr. 27, 1993

[54] INSECT REPELLENT COMPOSITIONS

[75] Inventor: Larry D. Nichols, Arlington, Mass.

[73] Assignee: Purepac, Inc., Elizabeth, N.J.

[21] Appl. No.: 875,198

[22] Filed: Apr. 24, 1992

Related U.S. Application Data

[63] Continuation of Ser. No. 619,721, Nov. 29, 1990, abandoned, which is a continuation-in-part of Ser. No. 358,690, May 30, 1989, Pat. No. 5,000,947.

[51] Int. Cl.$^5$ .................. A01N 25/12; A01N 37/44
[52] U.S. Cl. .................... 424/409; 424/488;
424/489; 424/499; 428/402.2; 514/781;
514/919; 514/561
[58] Field of Search ............ 424/405, 488, 489, 409

[56] References Cited

U.S. PATENT DOCUMENTS

| | | | |
|---|---|---|---|
| 3,824,085 | 7/1974 | Teno et al. | 44/7 B |
| 3,846,404 | 11/1974 | Nichols | 260/230 |
| 3,940,384 | 2/1976 | Teno et al. | 260/226 |
| 3,985,298 | 10/1976 | Nichols | 239/54 |
| 4,016,254 | 4/1977 | Seager | 423/33 |
| 4,024,073 | 5/1977 | Shimizu et al. | 252/316 |
| 4,029,726 | 6/1977 | Nichols | 264/41 |
| 4,067,824 | 1/1978 | Teno et al. | 252/522 |
| 4,128,507 | 12/1978 | Mitzner | 252/522 |
| 4,193,989 | 3/1980 | Teno et al. | 424/60 |
| 4,369,173 | 1/1983 | Causland et al. | 424/35 |
| 4,383,988 | 5/1983 | Teno et al. | 424/68 |
| 4,477,467 | 10/1984 | Nishizawa et al. | 424/69 X |
| 4,597,960 | 7/1986 | Cohen | 424/28 |
| 4,643,856 | 2/1987 | Nichols | 264/41 |
| 4,690,786 | 9/1987 | Ninomiya et al. | 264/4.6 |
| 4,690,825 | 9/1987 | Won | 424/501 |
| 4,695,464 | 9/1987 | Aldermann | 424/449 |
| 4,708,821 | 11/1987 | Shimokawa et al. | 512/12 |
| 4,724,240 | 2/1988 | Abrutyn | 514/847 |
| 4,738,851 | 4/1988 | Schoenwald et al. | 424/488 |
| 4,752,496 | 6/1988 | Fellows et al. | 432/27 |
| 4,755,433 | 7/1988 | Patel et al. | 428/422 |
| 4,762,718 | 8/1988 | Marks, Sr. | 424/405 X |
| 4,888,420 | 12/1989 | Steiner et al. | 536/64 |
| 4,925,667 | 5/1990 | Fellows et al. | 424/401 |
| 4,952,402 | 8/1990 | Sparks et al. | 424/419 |
| 5,000,947 | 3/1991 | Nichols | 424/69 |
| 5,013,473 | 5/1991 | Norbury et al. | 252/174.13 |

OTHER PUBLICATIONS

Moleculon, Inc., Form 10-K for FY ended Nov. 30, 1988, pp. 1-7.

Primary Examiner—Thurman K. Page
Assistant Examiner—Neil Levy
Attorney, Agent, or Firm—Thomas J. Engellenner; James E. Maslow

[57] ABSTRACT

Liquefiable powder compositions are disclosed for the delivery of topical insect repellents. In particular, microporous cellulosic powders, such as cellulose acetates or nitrates, are disclosed as high liquid content vehicles for the delivery of liquid insect or tick repellent preparations. The resulting powders permit the application of the arthropod repellent preparation by simply rubbing or brushing the formulation onto the skin, in such a manner that the powder liquefies and appears to vanish. Upon application, the frangible, liquid loaded cellulosic powders break up into minute particles that do not pass easily beyond the initial layers of the skin, but do permit the slow release of the insect repellent agent.

4 Claims, No Drawings

INSECT REPELLENT COMPOSITIONS

REFERENCE TO RELATED APPLICATION

This application is a continuation of U.S. Ser. No. 619,721, filed Nov. 29, 1990, now abandoned, which was a continuation-in-part of U.S. Serial No. 358,690 filed May 30, 1989, now U.S. Pat. No. 5,000,947.

BACKGROUND OF THE INVENTION

The technical field of this invention is the topical application of personal care agents and, in particular, methods and compositions for topical application of agents to repel insects and other arthropods.

In recent years the public has become increasingly aware that the bites of insects and arachnids is not only a severe nuisance in certain seasons and regions, it can also carry a life-threatening risk of infection with such illnesses as Lyme disease and equine encephalitis. (The term "insect" is used herein to encompass insects, ticks, arachnids and other nuisance or harmful arthropods, generally.)

One of the most effective first lines of defense against such bites, and one which causes little stress to environmentally beneficial arthropods, is the use of chemical repellents. A variety of repellents of diverse effectiveness have been used over the years, including such materials as citronella; safe and effective repellents in current use include N,N-diethyl-m-toluamide (DEET) and 2-ethyl-1,3-hexanediol (6–12)

Compositions useful as insect repellents should disperse easily onto the skin, adhere closely to the skin, resist penetration through the skin, and resist shedding with perspiration or rain. Unfortunately most insect repellents do not fully satisfy these requirements in terms of durability and prolonged residence on the skin. For example, DEET, used alone or compounded with common cosmetic extenders, gradually penetrates into deep layers of the skin where its insect-repelling activity is reduced.

There exists a need for better insect repellent compositions for more economical and reliable protection against the distress and danger of insect bites, tick bites and the bites of other arthropods.

SUMMARY OF THE INVENTION

Liquefiable polymer powder compositions are disclosed for the delivery of topical insect repellents In particular, microporous cellulosic powders, such as cellulose acetates or nitrates, are disclosed as high liquid content vehicles for the delivery of liquid insect and tick repellents to the skin. The resulting powders permit the application of an arthropod repellent preparation by simply rubbing or otherwise applying the formulation to the skin in such a manner than the powder liquefies and appears to vanish. Upon application the frangible, liquid-loaded cellulosic powder particles break up into minute fragments which do not pass beyond the superficial layers of the skin, but which do permit slow release of the repellent agent.

Details of the formation of cellulosic powders can be found in the above-referenced parent application, U.S. Ser. No. 358,690, filed May 30, 1989, U.S. Pat. No. 5,000,947 and a commonly-owned, copending application entitled "Process For Producing Liquid-Loaded Powders", by Larry D. Nichols and John F. Cline, filed contemporaneously herewith, both of which are incorporated herein by reference. A preferred polymer liquid-loadable powder includes microporous cellulose triacetate prepared by the method of the above application, entitled "Process For Producing Liquid-Loaded Powders".

In one technique, the liquefiable powders are formed by dissolving a cellulosic polymer and a pore-forming liquid in a volatile, polar solvent (e.g., a low molecular weight halogenated hydrocarbon, ester or diester) and then dispersively evaporating the solution, for example, by spray drying. Suitable volatile solvents for cellulosic polymers include methylene chloride, acetone, ethyl acetate, ethyl carbonate, methyl formate and the like. Methylene chloride is a preferred solvent when the cellulosic polymer is cellulose triacetate. Alternatively, other solvents, such as formic acid or the like, can be used and the resulting solution can be sprayed into a non-solvent such as methanol where the powder particles are then recovered by filtration and rinsing. The active agent can be incorporated into the solvent or introduced by liquid phase substitution after the powder is formed.

The cellulosic powders useful in the present invention can range from about one to about 500 microns in average diameter, preferably from about 5 to about 100 microns in average diameter, and typically are roughly microspherical in shape. They are further characterized by being microporous with interconnecting pores ranging in size from about one to about 500 nanometers and are capable of holding liquid payloads of active agents.

The cellulosic powder can be formed from cellulosic polymers chosen from the group of cellulose acetates, cellulose butyrates, cellulose nitrates, cellulose propionates, ethyl celluloses and discrete or molecular mixtures thereof. One preferred cellulosic powder is a polymeric powder of cellulose triacetate, having a (dry) acetyl content greater than about 42 percent. The liquid content of the cellulosic powders of the present invention can range from about 50 percent to about 95 percent by weight.

Compositions made in accordance with the present invention permit the delivery of effective amounts of active arthropod repellent ingredient without many of the problems normally associated with unconfined liquids and oils. By assisting in the distribution of repellent agents uniformly over the skin, and retarding the loss of such agents into the skin or off of the skin into the environment, the compositions of the invention enhance efficacy, improve economy and reduce the risk of adverse human or environmental reactions.

Arthropod repellents which can be used in the practice of the invention include N,N-diethyl-m-toluamide (DEET) and 2-ethyl-1,3-hexanediol (6–12) and derivatives or mixtures thereof, as well as other repellents known now or in the future to those skilled in the art. Liquid formulations containing 6–12 in a cellulosic liquefiable powder can be 100% active, or can contain extenders, emollients or diluents such as mineral oils, silicone oils, or fatty esters or alcohols Liquid formulations containing DEET in a liquefiable cellulosic powder can generally not be 100% active, since pure DEET is a powerful solvent and softening agent for many polymers, including cellulose esters and nitrates. Formulations containing as much as 65% DEET in inert liquids such as fatty esters and alcohols are acceptable and well tolerated by the polymer matrix.

In one embodiment the repellent agent can be incorporated into frangible cellulosic microbeads or other powder forms, and then formulated into a cream or lotion type vehicle by mixture with a liquid base. Alternatively the compositions can be formulated as loose powders, compacted into cakes, blended into binders and shaped into bars or application sticks.

Suitable liquid bases for cream or lotion type embodiments include water, mineral or silicone oils, volatile silicones, and moisturizing agents such as glycerin or propylene glycol.

Regardless of the embodiment, various additives can be mixed together with the liquid loaded microcapsules (or liquid base) including, for example, talc, cornstarch, waxes, silicones, analgesics, cosmetics, fragrances, lubricants, emollients, moisturizers, medications and other personal care agents, colorants, pearlescent agents, and mixtures of such additives.

In the compacted cake embodiments, the liquid loaded powders can be compacted to packing densities ranging from about 55 percent to about 75 percent, more preferably from about 60 percent to about 70 percent of the void-free density of the combined materials to yield cakes that are dry and firm and yet readily permit transfer of the formulation to the skin by finger or brush.

Such compacted cakes can be obtained by applying a pressure ranging from about 50 to about 80 PSI to a cellulosic powder which has been appropriately loaded with a liquid payload of the active agent. In the absence of other additives, the resulting shaped articles have a compacted density ranging from about 0.55 to about 0.75 gm/cc.

Sticks or bars incorporating liquefiable powders with active agent payloads can be made by a variety of techniques. For example, sticks can be formulated by compounding a liquefiable powder with fatty alcohols, fatty acids, and/or salts of fatty acid anions with metallic or alkanolamine cations to produce a stick having a soap as the binding agent.

Alternatively, stick compositions can be formed by compounding a liquefiable powder with soft water-soluble polymers, such as polyethylene glycols or polypropylene glycols, to produce a stick having a soluble wax as the binding agent. Sticks can also be made up by compounding a liquefiable powder with silicones or with blends of liquids and solids, such micronized aluminum antiperspirant salts and/or propylene glycols, to produce sticks having a thick or partially solidified slurry as the binding agent In yet another approach, sticks can be formed by compounding a liquefiable powder with a fusible wax, such as myristyl myristate, and then applying heat and pressure to produce sticks having a fatty ester wax as the binding agent.

The above binding agents can be introduced directly, or as payload in a second portion of liquefiable powder to be blended with that carrying the active ingredient. Other methods of stick production will readily occur to those skilled in the art.

The invention will next be described in connection with certain exemplary methods and compositions. However, it should be clear that various additions, subtractions and changes can be made by those skilled in the art without departing from the spirit or scope of the invention. For example, although the illustrative examples describe the use of DEET and 6–12 as the active agents, various other insect repellents can be dissolved or dispersed within the liquid phase of the cellulosic powder to provide similar insect repellent action.

In some applications, it may also be preferable to include a quantity of a dry cellulosic powder (e.g., less than 50 percent of the total cellulosic components) to provide additional structural integrity to the composition. The term "dry cellulosic powder" is used herein to describe powders whose internal pores are liquid-free or have a liquid content of less than 50 percent.

DETAILED DESCRIPTION

The examples below illustrate the preparation of liquefiable arthropod repellent loaded powders.

EXAMPLE 1

A liquefiable powder was prepared by spray evaporative drying. A liquid porogen was prepared from 60 parts by weight of N,N-diethyl-m-toluamide (DEET) and 40 parts by weight of 2-octyldodecanol, a heavy secondary alcohol commonly used in cosmetic formulations. 40 grams of cellulose triacetate was dissolved in 3000 gm of methylene chloride by moderate stirring for 4 hours. To that solution was added 460 gm of the previously prepared porogen diluted with 1000 gm of methylene chloride. The resulting homogeneous solution was sprayed at 1000 PSI from a 0.0135" nozzle, downward into a tower 100 cm in diameter and 300 cm tall, through which 1250 liters per minute of solvent-free air was passing from top to bottom.

The evaporatively-formed powder was collected on a fabric filter spanning the bottom of the tower, and the solvent-laden air was passed through carbon beds to collect and recover solvent. The product was transferred to a steel tray and exposed as a 1 cm deep layer in a ventilated hood for 25 minutes to remove residual solvent. Analysis showed 8% cellulose triacetate, 36.8% octyldodecanol, and 55.2% DEET, with less than 5 ppm or residual methylene chloride.

The resulting white powder could be readily dusted onto the skin and made to liquefy and vanish by gentle rubbing. There was no perceptible grit or gumminess.

EXAMPLE 2

A powder like that of example 1 was prepared using as a porogen pure 2-ethyl-1,3-hexanediol (6–12) insect repellent. The powder analyzed to contain 8.1% cellulose acetate and 91.9% 6–12 liquid, with less than 1 ppm of methylene chloride.

It will be understood that the above description pertains to only several embodiments of the present invention. That is, the description is provided by way of illustration and not by way of limitation. The invention, therefore, is to be defined according to the following claims.

What I claim is:

1. An insect repellent composition for the delivery of a topical insect repellent, the composition comprising a formulation of a frangible, liquid-containing, cellulosic powder formed by spray evaporation and having particles ranging in average diameter from about 1 to about 500 micrometers, the particles further characterized by being microporous with a plurality of interconnecting pores ranging in size from about 1 to about 500 nanometers and having a structure which is readily fragmented and a liquid insect repellent preparation loaded within the pores of the powder particles, such that the liquid-containing powder has a liquid content ranging from about 50 percent to about 95 percent by weight, and, upon application and rubbing, the rubbed particles fragment and the insect repellent preparation is readily released.

2. The composition of claim 1 wherein the cellulosic powder is a polymeric powder chosen from the group consisting of cellulose acetates, cellulose butyrates, cellulose nitrates, cellulose propionates, ethyl celluloses, and discrete ad molecular mixtures thereof.

3. The composition of claim 1 wherein the liquid insect repellent preparation comprises an insect repellent compound chosen from the group consisting essentially of N,N-diethyl-m-toluamide 2-ethyl-1,3- hexanediol, derivatives and mixtures thereof.

4. The composition of claim 1 wherein the composition further comprises a liquid not incorporated within the frangible powder.

* * * * *

UNITED STATES PATENT AND TRADEMARK OFFICE
CERTIFICATE OF CORRECTION

PATENT NO. : 5,206,022
DATED : April 27, 1993
INVENTOR(S) : Larry D. Nichols

It is certified that error appears in the above-identified patent and that said Letters Patent is hereby corrected as shown below:

On title page, item [73] should read as follows:

--PurePac, Inc., Elizabeth, N.J.--

Signed and Sealed this

Eighteenth Day of January, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,206,022
DATED : April 27, 1993
INVENTOR(S) : Larry D. Nichols

It is certified that error appears in the above-identified patent and that said Letters Patent is hereby corrected as shown below:

On the Title Page:
Please amend the above-referenced patent so that Page 1, [73] Assignee reads:

--PUREPAC, INC., Elizabeth, N.J.--

This certificate supersedes Certificate of Correction issued Jan. 18, 1994.

Signed and Sealed this

Second Day of August, 1994

*Attest:*

BRUCE LEHMAN

*Attesting Officer*   *Commissioner of Patents and Trademarks*